United States Patent
Merlet et al.

(10) Patent No.: US 10,478,143 B2
(45) Date of Patent: Nov. 19, 2019

(54) SYSTEM AND METHOD OF GENERATING AND UPDATNG A THREE DIMENSIONAL MODEL OF A LUMINAL NETWORK

(71) Applicant: COVIDIEN LP, Mansfield, MA (US)

(72) Inventors: Nicolas J. Merlet, Ramot Bet (IL); Oren P. Weingarten, Herzliya (IL)

(73) Assignee: COVIDIEN LP, Mansfield, MA (US)

( * ) Notice: Subject to any disclaimer, the term of this patent is extended or adjusted under 35 U.S.C. 154(b) by 473 days.

(21) Appl. No.: 15/226,111

(22) Filed: Aug. 2, 2016

(65) Prior Publication Data

US 2018/0035966 A1 Feb. 8, 2018

(51) Int. Cl.
*A61B 6/00* (2006.01)
*A61B 90/10* (2016.01)
(Continued)

(52) U.S. Cl.
CPC .......... *A61B 6/5235* (2013.01); *A61B 1/2676* (2013.01); *A61B 6/032* (2013.01);
(Continued)

(58) Field of Classification Search
CPC .......... A61B 6/5235; A61B 2090/3983; A61B 2090/3966; A61B 2034/2068; A61B 6/032; A61B 6/12; A61B 6/4441; A61B 6/466; A61B 6/487; A61B 6/463; A61B 6/5205; A61B 34/20; A61B 90/10; A61B 1/2676; G06T 7/33; G06T 7/0012
See application file for complete search history.

(56) References Cited

U.S. PATENT DOCUMENTS 5,951,475 A * 9/1999 Gueziec ................ G06T 3/0068
128/922
6,188,355 B1 2/2001 Gilboa
(Continued)

FOREIGN PATENT DOCUMENTS

| EP | 1278458 B1 | 7/2011 |
|---|---|---|
| WO | 0010456 A1 | 3/2000 |
| WO | 0167035 A1 | 9/2001 |

OTHER PUBLICATIONS

International Search Report for application No. PCT/US2017/044803 dated Oct. 26, 2017 (12 pages).

*Primary Examiner* — Carolyn A Pehlke

(57) ABSTRACT

A method of updating a model of a luminal network. The method includes performing first imaging of a target, generating 3D image data including locations of fiducial markers using images captured in the first imaging, performing second imaging of the target from a first viewpoint and a second viewpoint, generating 2D image data including locations of the fiducial markers from the first viewpoint and the second viewpoint using images captured in the second imaging, determining locations of the fiducial markers in 3D space according to locations of the fiducial markers within the 2D image data of the first viewpoint, locations of the fiducial markers within the 2D image data of the second viewpoint, and the known angle, and registering the 3D image data generated using images captured in the first imaging with the determined locations of the fiducial markers in 3D space. The first viewpoint and the second viewpoint are oriented at a known angle relative to each other.

11 Claims, 9 Drawing Sheets

(51) Int. Cl.
*A61B 6/03* (2006.01)
*A61B 34/20* (2016.01)
*A61B 6/12* (2006.01)
*A61B 1/267* (2006.01)
*G06T 7/33* (2017.01)
*A61B 90/00* (2016.01)
*A61B 34/10* (2016.01)

(52) U.S. Cl.
CPC .............. *A61B 6/12* (2013.01); *A61B 6/4441* (2013.01); *A61B 6/466* (2013.01); *A61B 6/487* (2013.01); *A61B 34/20* (2016.02); *A61B 90/10* (2016.02); *G06T 7/33* (2017.01); *A61B 6/463* (2013.01); *A61B 6/5205* (2013.01); *A61B 2034/107* (2016.02); *A61B 2034/2065* (2016.02); *A61B 2034/2068* (2016.02); *A61B 2090/3966* (2016.02); *A61B 2090/3983* (2016.02); *G06T 2207/10081* (2013.01); *G06T 2207/10121* (2013.01); *G06T 2207/30061* (2013.01)

(56) References Cited

U.S. PATENT DOCUMENTS

| | | | |
|---|---|---|---|
| 7,697,972 B2 | 4/2010 | Verard et al. | |
| 7,901,348 B2 | 3/2011 | Soper et al. | |
| 8,239,001 B2 | 8/2012 | Verard et al. | |
| 8,565,858 B2 | 10/2013 | Gilboa | |
| 8,821,376 B2 | 9/2014 | Tolkowsky | |
| 9,265,468 B2 | 2/2016 | Rai et al. | |
| 2004/0082870 A1* | 4/2004 | Rudy | A61B 5/0402 600/509 |
| 2007/0060799 A1* | 3/2007 | Lyon | A61B 34/20 600/300 |
| 2008/0137931 A1* | 6/2008 | Drumm | A61B 6/022 382/131 |
| 2010/0003006 A1 | 1/2010 | Tokunaka | |
| 2011/0085720 A1 | 4/2011 | Averbuch | |
| 2012/0059248 A1 | 3/2012 | Holsing et al. | |
| 2012/0289825 A1 | 11/2012 | Rai et al. | |
| 2013/0223702 A1 | 8/2013 | Holsing et al. | |
| 2014/0046315 A1 | 2/2014 | Ladtkow et al. | |
| 2014/0270441 A1 | 9/2014 | Baker | |
| 2014/0275985 A1 | 9/2014 | Walker et al. | |
| 2014/0281961 A1 | 9/2014 | Baker | |
| 2014/0282216 A1 | 9/2014 | Baker | |
| 2014/0313196 A1* | 10/2014 | Mistretta | G06T 11/008 345/424 |
| 2015/0138186 A1* | 5/2015 | Carrell | F24C 15/2021 345/419 |
| 2015/0141809 A1 | 5/2015 | Costello et al. | |
| 2015/0265257 A1 | 9/2015 | Costello et al. | |
| 2016/0000302 A1 | 1/2016 | Brown et al. | |
| 2016/0000356 A1 | 1/2016 | Brown et al. | |
| 2016/0005168 A1 | 1/2016 | Merlet | |

* cited by examiner

SYSTEM AND METHOD OF GENERATING AND UPDATNG A THREE DIMENSIONAL MODEL OF A LUMINAL NETWORK

BACKGROUND

Technical Field

The present disclosure relates to bronchial registration and, more particularly, to devices, systems, and methods for updating a three-dimensional bronchial tree model with fluoroscopic projections.

Description of Related Art

Standard of care for lung diseases, such as asthma, chronic obstructive pulmonary disease (COPD), and chronic obstructive lung disease (COLD), and other lung-related diseases has been focused largely on medical procedures such as resection and lobectomies which are highly invasive to patients. And while medicinal therapies have been developed these tend to focus on cancer treatments such as chemotherapy drugs.

Electromagnetic navigation (EMN) has helped expand the possibilities of treatment of luminal networks such as the lungs. EMN relies on non-invasive imaging technologies, such as computed tomography (CT) scanning and magnetic resonance imaging (MRI) to generate 3-dimensional models of a luminal network. EMN in combination with these non-invasive imaging technologies has been also used to identify a location of a target and to help clinicians navigate a luminal network of the lung to the target. CT and MRI procedures come with certain drawbacks. CT imaging cannot be used in real time due to a long reconstruction time and the radiation hazard to the physicians. MRI similarly cannot be used in real time as the MRI housing restricts space to perform a procedure and metallic items cannot be used around an MRI.

As an alternative to CT and MRI, fluoroscopic imaging may be used to provide real-time imaging capabilities. However, fluoroscopic images, while useful, present certain drawbacks for navigation. Using fluoroscopic imaging, it is often difficult to distinguish luminal passageways from solid tissue. Moreover, images generated by the fluoroscope are two-dimensional whereas navigating the airways of a patient requires the ability to maneuver in three dimensions.

Therefore, there is a need for an imaging process and system that combines CT or MRI imaging with fluoroscopic imaging to provide a 3D rendering of a patient's luminal network with the requisite resolution while also updating the 3D model in real time using imaging modalities that can only produce 2D image data.

SUMMARY

Provided in accordance with the present disclosure is a method of updating a model of a luminal network. The method includes performing first imaging of a target, generating 3D image data including locations of fiducial markers using images captured in the first imaging, performing second imaging of the target from a first viewpoint and a second viewpoint, generating 2D image data including locations of the fiducial markers from the first viewpoint and the second viewpoint using images captured in the second imaging, determining locations of the fiducial markers in 3D space according to locations of the fiducial markers within the 2D image data of the first viewpoint, locations of the fiducial markers within the 2D image data of the second viewpoint, and the known angle, and registering the 3D image data generated using images captured in the first imaging with the determined locations of the fiducial markers in 3D space. The first viewpoint and the second viewpoint are oriented at a known angle relative to each other.

In an aspect of the present disclosure, the first imaging is performed using CT imaging.

In another aspect of the present disclosure, the second imaging is performed using fluoroscopic imaging.

In yet another aspect of the present disclosure, determining locations of the fiducial markers in 3D space includes projecting rays from the first viewpoint through endpoints of each fiducial marker, projecting rays from the second viewpoint through the endpoints of each fiducial marker, determining intersections of the rays projected from the first source and the rays projected from the second source as locations of fiducial marker endpoints in 3D space.

In a further aspect of the present disclosure, the method further includes determining a distance between adjacent fiducial marker endpoints and comparing the distance between adjacent fiducial marker endpoints with a known length of the fiducial marker.

In an aspect of the present disclosure, the method further includes determining movement distances between fiducial marker locations in 3D space and fiducial marker locations in the 3D image data from the first imaging.

In a further aspect of the present disclosure, updating the 3D image data includes determining which movement distance is greatest and registering the 3D image data generated using images captured in the first imaging with the determined locations of the fiducial markers in 3D space without the location in 3D space of the fiducial marker corresponding to the greatest movement distance.

In another aspect of the present disclosure, updating the 3D image data includes determining a distance of each fiducial marker from the treatment target, weighting each fiducial marker according to its distance from the treatment target, and registering the 3D image data generated using images captured in the first imaging with the determined locations of the fiducial markers in 3D space according to the weight of each fiducial marker.

In another aspect of the present disclosure, the method further includes determining a distance of each fiducial marker from the treatment target, weighting each fiducial marker according to its distance from the treatment target, and registering the 3D image data generated using images captured in the first imaging with the determined locations of the fiducial markers in 3D space according to the weight of each fiducial marker.

In another aspect of the present disclosure, the method further includes measuring changes in location of fiducial markers in the 3D image data generated using images captured in the first imaging before and after registration, and determining a target error based on changes in location of fiducial markers in the 3D image data.

In a further aspect of the present disclosure, the method further includes excluding, from the determination of target error, changes in location of fiducial markers in the 3D image data where the change in the location of the fiducial marker exceeds a threshold value.

Provided in accordance with the present disclosure is a system including a display and a computing device including a processor and a memory. The display is configured to display 3D image data of a target area, first 2D image data of the target imaged from a first viewpoint, and second 2D image data of the target imaged from a second viewpoint.

The 3D image data includes locations of fiducial markers. The second viewpoint oriented at a known angle from the first viewpoint. The memory stores instructions which, when executed by the processor, cause the computing device to determine locations of the fiducial markers in 3D space according to locations of the fiducial markers within first 2D image data, second 2D image data, and the known angle, and update the 3D image data with the determined locations of the fiducial markers in 3D space.

In an aspect of the present disclosure, the 3D image data is generated using CT imaging.

In another aspect of the present disclosure, the first and second 2D image data are using fluoroscopic imaging.

In another aspect of the present disclosure, in the determination of locations of the fiducial markers in 3D space, the instructions further cause the computing device to project rays from the first viewpoint through endpoints of each fiducial marker, project rays from the second viewpoint through the endpoints of each fiducial marker, and determine intersections of the rays projected from the first source and the rays projected from the second source as locations of fiducial marker endpoints in 3D space.

In another aspect of the present disclosure, the instructions further cause the computing device to determine a distance between adjacent fiducial marker endpoints, and compare the distance between adjacent fiducial marker endpoints with a known length of the fiducial marker.

In yet another aspect of the present disclosure, the instructions further cause the computing device to determine movement distances between fiducial marker locations in 3D space and fiducial marker locations in the 3D image data.

In a further aspect of the present disclosure, the instructions further cause the computing device to determine which movement distance is greatest and register the 3D image data with the determined locations of the fiducial markers in 3D space without the location in 3D space of the fiducial marker corresponding to the greatest movement distance.

In a further aspect of the present disclosure, the instructions further cause the computing device to determine a distance of each fiducial marker from the treatment target, weight each fiducial marker according to its distance from the treatment target, and register the 3D image data with the determined locations of the fiducial markers in 3D space according to the weight of each fiducial marker.

In another aspect of the present disclosure, the instructions further cause the computing device to measure changes in location of fiducial markers in the 3D image data generated using images captured in the first imaging before and after registration, and determine a target error based on changes in location of fiducial markers in the 3D image data.

In another aspect of the present disclosure, the instructions further cause the computing device to exclude, from the determination of target error, changes in location of fiducial markers in the 3D image data where the change in the location of the fiducial marker exceeds a threshold value.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
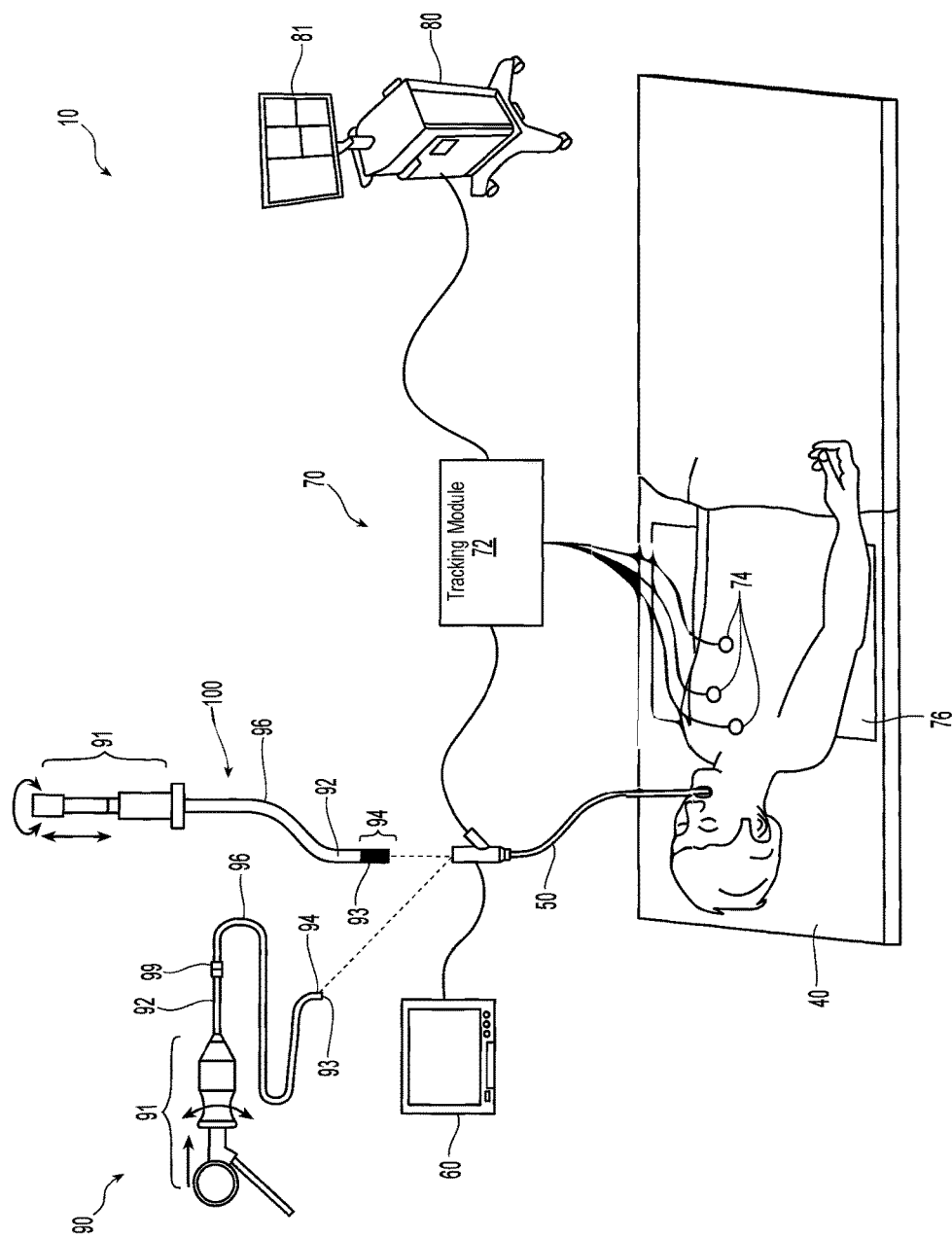
FIG. 1 is a perspective view of an electromagnetic navigation system in accordance with the present disclosure.

The present disclosure is directed to devices, systems, and methods for generating and updating a three dimensional model of a luminal network. More particularly, the disclosure relates to modifying a three-dimensional model of a patient's lungs using two or more two-dimensional images by capturing and comparing common features or indicators observable in both the three-dimensional model and the two-dimensional images.

A physician may perform a CT scan of a patient's airways to generate a three-dimensional model to aid the clinician in navigating the lungs. A patient's lungs, however, are not static. The lungs move during a typical respiration cycle in a normative pattern. Over time, the positions of various elements of the lungs migrate and change position, compromising the accuracy of the CT scan. While the CT scan may provide a model of the lungs accurate enough to allow a physician to navigate near a treatment target, a higher degree of accuracy is necessary to navigate to a treatment target near outermost positions of the bronchial tree and to remain at the treatment target throughout the intended treatment procedure.

In order to increase the accuracy of the three-dimensional model, a physician may guide a bronchoscopic navigation catheter near the treatment target to place fiducial markers that are observable using CT imaging and fluoroscopic imaging. In accordance with one embodiment of the present disclosure, after performing a CT scan on the patient's airways, 3D data and a 3D model including fiducial marker locations are generated. During, or just prior to, a procedure, the airways, including the fiducial markers placed within, are imaged again using fluoroscopic imaging from at least two orientations. By selectively comparing locations of the fiducial markers in the 3D data and model with locations of the fiducial markers within the fluoroscopic images, the 3D model may be updated immediately preceding or in real time during the procedure.

The updated 3D model may be useful for performing an electromagnetic navigation (EMN). An EMN generally involves at least two phases: (1) planning a pathway to a target located within, or adjacent to, the patient's lungs; and (2) navigating a probe to the target along the planned pathway. These phases are generally referred to as (1)

"planning" and (2) "navigation." An example of the planning software can be found in commonly assigned U.S. Provision Patent Application No. 62/020,240 entitled "SYSTEM AND METHOD FOR NAVIGATING WITHIN THE LUNG" the entire contents of which are incorporated herein by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the EMN.

With reference to FIG. 1, an EMN system 10 suitable for implementing methods for planning and performing treatment of an area of a patient's lungs and placing fiducial markers is provided in accordance with the present disclosure. One such EMN system 10 is the ELECTROMAGNETIC NAVIGATION BRONCHOSCOPY® system currently sold by Covidien™ LP. As shown in FIG. 1, EMN system 10 is used to perform one or more procedures on a patient supported on an operating table 40. In this regard, EMN system 10 generally includes a bronchoscope 50, monitoring equipment 60, an electromagnetic (EM) tracking system 70, and a computing device or workstation 80.

Bronchoscope 50 is configured for insertion through the patient's mouth and/or nose into the patient's airways. As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, for example, a video display, for displaying the video images received from the video imaging system of bronchoscope 50.

In an embodiment, bronchoscope 50 may operate in conjunction with a catheter guide assembly, two types of which are depicted in FIG. 1 (for example, catheter guide assemblies 90, 100). Catheter guide assemblies 90, 100, including a locatable guide (LG) 92 and an extended working channel (EWC) 96, are configured for insertion through a working channel of bronchoscope 50 into the patient's airways (although the catheter guide assemblies 90, 100 may alternatively be used without bronchoscope 50). Although configured differently, catheter guide assemblies 90, 100 share a number of common components. Specifically, each catheter guide assembly 90, 100 includes a handle 91, which is connected to the EWC 96. In each assembly 90, 100, EWC 96 is sized for placement into the working channel of bronchoscope 50. In the operation of each assembly 90, 100, the LG 92, including an EM sensor 94, is inserted into EWC 96 and locked into position such that EM sensor 94 extends a desired distance beyond the distal tip 93 of EWC 96. The location of EM sensor 94, and thus the distal end of EWC 96, within an EM field generated by EM field generator 76 can be derived by tracking module 72, and computing device 80. Catheter guide assemblies 90, 100 may have different operating mechanisms, but each includes handle 91 that can be manipulated by rotation and compression to steer distal tip 93 of LG 92 and EWC 96.

Catheter guide assembly 90 is currently marketed and sold by Covidien™ LP under the name SUPERDIMENSION® Procedure Kits. Catheter guide assembly 100 is currently sold by Covidien™ LP under the name EDGE™ Procedure Kits. Both kits include handle 91, EWC 96, and LG 92. For a more detailed description of catheter guide assemblies 90, 100, reference is made to commonly-owned U.S. Patent Publication No. 2014/0046315, entitled "MICROWAVE ABLATION CATHETER AND METHOD OF UTILIZING THE SAME", filed on Mar. 15, 2013 by Ladtkow et al., the entire contents of which are hereby incorporated by reference.

LG 92 and EWC 96 are selectively lockable relative to one another via a locking mechanism 99. A six degrees-of-freedom EM tracking system 70, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dec. 14, 1998 by Gilboa, the entire contents of each of which is incorporated herein by reference, or any other suitable positioning measuring system, is utilized for performing navigation, although other configurations are also contemplated.

EM tracking system 70 may be configured for use with catheter guide assemblies 90, 100 to track the position of EM sensor 94 as it moves in conjunction with EWC 96 through the airways of the patient, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes application 81, where the data from sensors 74 are used to calculate a patient coordinate frame of reference.

According to an embodiment, catheter guide assemblies 90, 100 are configured to receive a biopsy, ablation, or other types of surgical tools following navigation to a target location and removal of LG 92. Surgical tools may be used to collect one or more tissue sample from the target location, apply energy to the target location, or perform similar functions. An embodiment, tracking system 70 may be configured in conjunction with a surgical tool to facilitate navigation of the tool to the target location, and tracking of a location of the tool as it is manipulated relative to the target location to obtain the tissue sample.

For example, a variety of useable tools are described in U.S. Patent Publication No. 2015/0141809, entitled "DEVICES, SYSTEMS, AND METHODS FOR NAVIGATING A BIOPSY TOOL TO A TARGET LOCATION AND OBTAINING A TISSUE SAMPLE USING THE SAME", filed Sep. 17, 2014, by Costello et al., and U.S. Patent Publication No. 2015/0265257, entitled "DEVICES, SYSTEMS, AND METHODS FOR NAVIGATING A BIOPSY TOOL TO A TARGET LOCATION AND OBTAINING A TISSUE SAMPLE USING THE SAME", filed Dec. 9, 2014, by Costello et al., the contents of each of which are incorporated herein by reference and useable with the EMN system 10 as described herein.

Computing device 80 includes software and/or hardware, such as an EMN application 81, used to facilitate the various phases of an EMN procedure, including generating the 3D model, identification of a target location, planning a pathway to the target location, registration of the 3D model with the patient's actual airways, and navigation to the target location. For example, during procedure planning, computing device 80 utilizes computed tomographic (CT) scan, magnetic resonance imaging (MRI) scan, and/or positron emission tomography (PET) scan image data for generating and viewing the 3D model of the patient's airways, enables the identification of a target location on the 3D model (automatically, semi-automatically or manually), and allows for the determination and selection of a pathway through the patient's airways to the target location. While the CT scan image data may have gaps, omissions, and/or other imperfections included in the image data, the 3D model is a smooth representation of the patient's airways, with any such gaps, omissions, and/or imperfections in the CT scan image data filled in or corrected. The 3D model may be presented on a display monitor associated with computing device 80, or in any other suitable fashion. An example of the planning software described herein can be found in U.S. Patent Publication Nos. 2014/0281961, 2014/0270441, and 2014/0282216, filed by Baker et al. on Mar. 15, 2013, and entitled "PATHWAY PLANNING SYSTEM AND METHOD", the contents of all of which are incorporated herein by reference. Further examples of the planning software can be found in commonly assigned U.S. patent application Ser. No. 14/753,288, entitled "SYSTEM AND METHOD FOR NAVIGATING WITHIN THE LUNG", filed on Jun. 29, 2015, by Brown et al., the contents of which are incorporated herein by reference.

Using computing device 80, various views of the 3D model may be presented and may be manipulated by a clinician to facilitate identification of a target location and selection of a suitable pathway through the patient's airways to access the target location. As noted above, the target location may be a surgical site where the treatment is to be performed, and/or a portion of or entire lobe of the patient's lungs requiring treatment. The 3D model may include, among other things, a model airway tree corresponding to the actual airways of the patient's lungs, and showing the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleura and fissures of the lungs. Some or all of the aforementioned elements may be selectively displayed, such that the clinician may choose which elements should be displayed when viewing the 3D model. For example, EMN application 81 may be configured in various states to display the 3D model in a variety of view modes. For each view of the 3D model, the angle from which the 3D model is displayed may correspond to a view point. The view point may be fixed at a predefined location and/or orientation, or may be adjusted by the clinician operating computing device 80.

Computing device 80, via application 81, may further be configured to review the plan created by the clinician to determine if the plan accounts for all detected abnormalities in the lungs of the patient. For example, an abnormality may be detected where a lung fissure is determined to be partially incomplete or entirely absent. An abnormality may also be detected if airways, blood vessels, and/or lymphatic lumens from one lung lobe have fused with airways, blood vessels, or lymphatic lumens from another lung lobe, and thereby breached the division between the lung lobes. If computing device 80 determines that the plan created by the clinician does not account for all detected abnormalities, adjustments to the plan may be determined and presented to the clinician for review.

Following planning, a procedure may be undertaken in which EM sensor 94, in conjunction with tracking system 70, enables tracking of EM sensor 94 (and thus the distal end of EWC 96 or a surgical tool) as EM sensor 94 is advanced through the patient's airways following the pathway planned during the planning phase. As an initial step of the procedure, the 3D model is registered with the patient's actual airways. One potential method of registration involves navigating LG 92 into each lobe of the patient's lungs to at least the second bifurcation of the airways of that lobe. The position of LG 92 is tracked during this registration phase, and the 3D model is iteratively updated based on the tracked position of the locatable guide within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. patent application Ser. No. 14/790,581 entitled "REAL-TIME AUTOMATIC REGISTRATION FEEDBACK", filed on Jul. 2, 2015, by Brown et al., the contents of each of which are incorporated herein by reference. While the registration process focuses on aligning the patient's actual airways with the airways of the 3D model, registration also ensures that the position of vascular structures, pleura, and fissures of the lungs are accurately determined.

Figure 2:
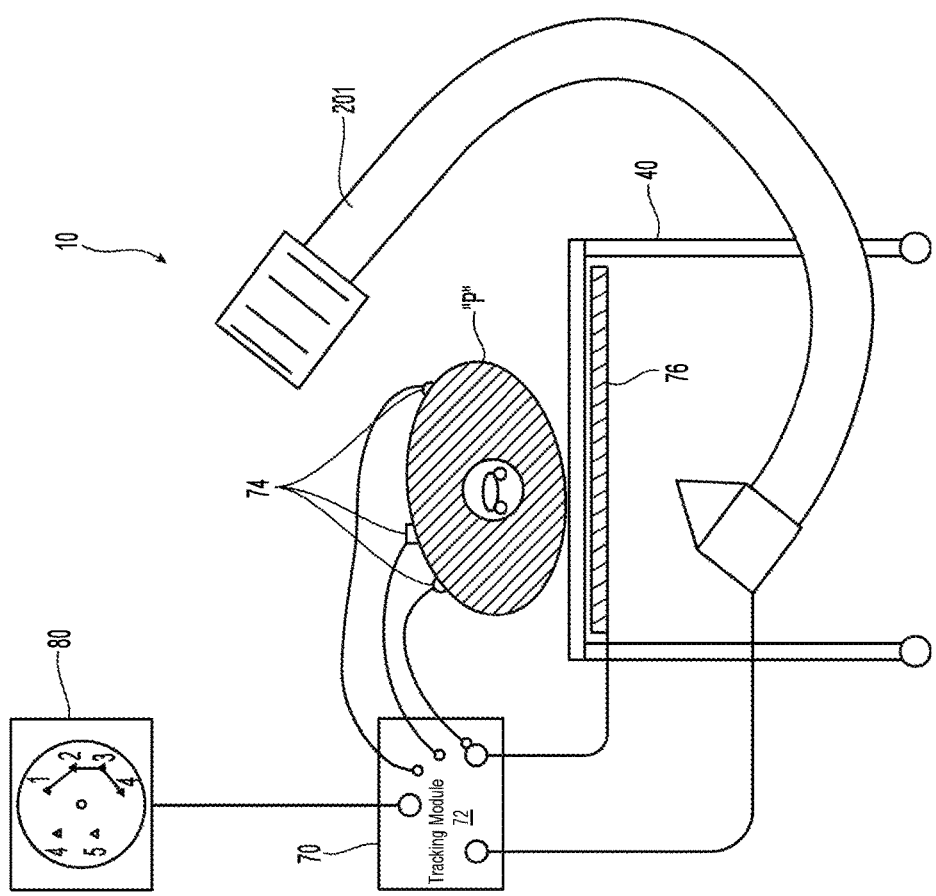
FIG. 2 is an end view of a fluoroscopic imaging C-arm incorporated in the EMN system of FIG. 1.

FIG. 2 depicts another view of the EMN system 10, including a fluoroscopic imaging device 201 capable of acquiring fluoroscopic or x-ray images or video of the patient "P." The images, series of images, or video captured may be stored within the imaging device 201 or transmitted to workstation 80 for storage, processing, and display. Additionally, the imaging device 201 may rotate about the patient "P" so that images may be acquired from different angles or perspectives relative to the patient "P." Imaging device 201 may include a single imaging device or more than one imaging device. In embodiments including multiple imaging devices, each imaging device may be a different type of imaging device or the same type. Further details regarding the imaging device 201 are described in U.S. Pat. No. 8,565,858, which is incorporated by reference in its entirety herein.

Figure 3:
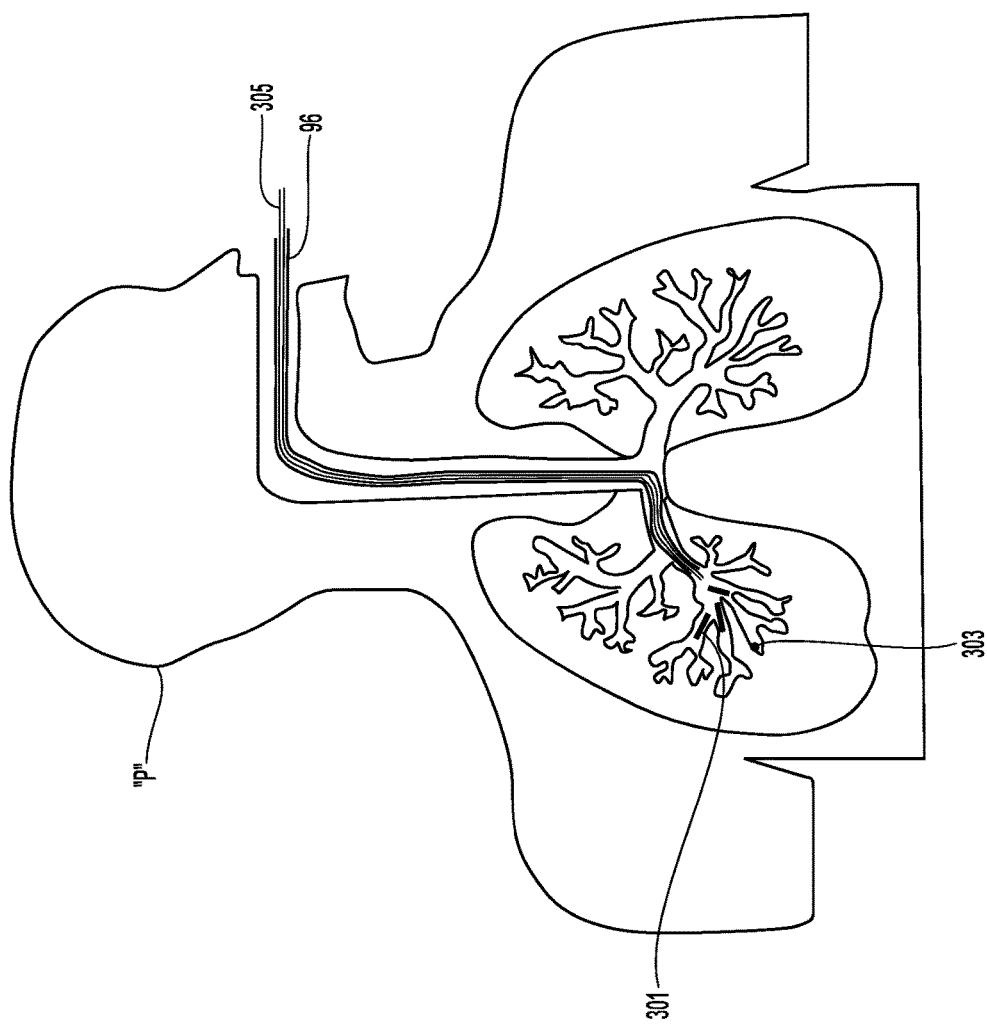
FIG. 3 is a schematic view of fluoroscopic markers positioned near a treatment target within a bronchus of the patient.

Turning to FIG. 3, there is shown a schematic view of fluoroscopic markers 301 positioned near a treatment target 303 within a bronchus of the patient. FIG. 3 further shows EWC 96 within the trachea of the patient with a guide wire 305 within EWC 96 and extending distally beyond distal tip 93 of the EWC 96 into a branch of the bronchial tree. Marker 301 is guided through EWC 96 using guide wire 305 to a location near treatment target 303. When guide wire 305 reaches a position near target 303, appropriately distanced from other fluoroscopic markers 301, guide wire 305 releases fluoroscopic marker 301. Fluoroscopic markers 301 are distributed as equally as possible about the target to allow for a complete analysis of lung movement near treatment target 303. As will be appreciated, other mechanisms, systems, and methods for deploying fluoroscopic markers can be used without departing from the scope of the present disclosure.

Figure 4:
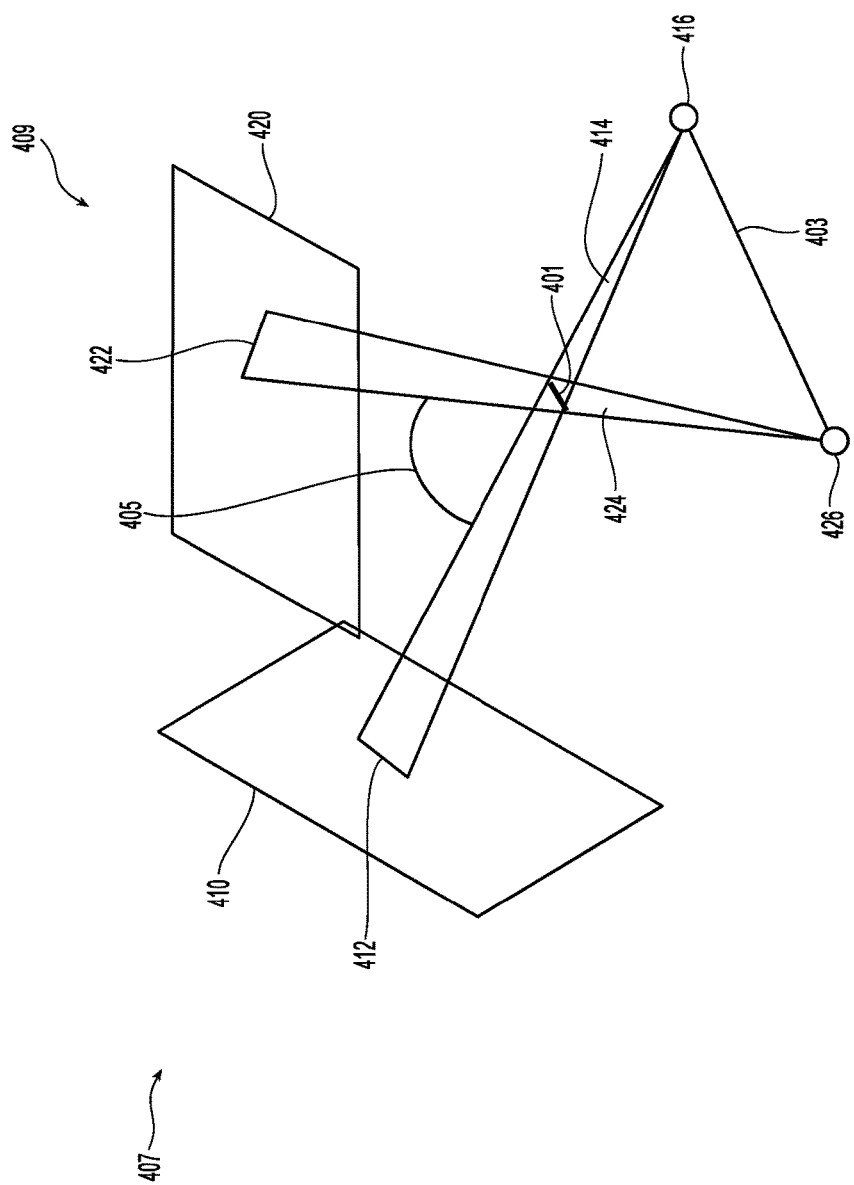
FIG. 4 is three-dimensional diagram view of a process of locating a fluoroscopic marker between two fluoroscopic images.

Referring now to FIG. 4, a three-dimensional diagram view of a process of locating a fluoroscopic marker between two fluoroscopic images is shown. FIG. 4 includes a first fluoroscopic view 407, a second fluoroscopic view 409, an angle 405 between fluoroscopic views 407, 409, and a 3D translation 403 between fluoroscopic views 407, 409. Fluoroscopic views 407, 409 are projected in 3D space and transposed relative to one another according to known angle 405 and initially according to assumed reasonable values for image diameter, pixel-to-mm ratio and source-to-imagedistance. The orientation of fluoroscopic views 407, 409 is adapted over time according to pose estimation and other manipulations.

First fluoroscopic view 407 includes a first fluoroscopic image 410, a first fluoroscopic 2D marker location 412 in first fluoroscopic image 410, a first fluoroscopic projection 414 of first fluoroscopic 2D marker location 412, and a first fluoroscopic imager 416. Second fluoroscopic view 409 includes a second fluoroscopic image 420, a second fluoroscopic 2D marker location 422 in second fluoroscopic image 420, a second fluoroscopic projection 424 of second fluoroscopic marker location 422 in second fluoroscopic image 420, and a second fluoroscopic imager 426. Fluoroscopic projections 414, 424 project from fluoroscopic imagers 416, 426 to endpoints of fluoroscopic 2D marker locations 412, 422. Fluoroscopic 2D marker locations 412, 422 represent angular 2D projections of fluoroscopic marker 301. Where fluoroscopic projections 414, 424 intersect, there is shown a 3D fluoroscopic marker position 401. 3D fluoroscopic marker position 401 represents an estimate of the 3D location of fluoroscopic marker 301. 3D fluoroscopic marker position 401 depends on known angle 405 and adjustable 3D translation 403. Fluoroscopic views 407, 409 may be adjusted in order to modify the size and location of 3D fluoroscopic marker position 401. In turn, comparing the accuracy of 3D fluoroscopic marker position's 401 size and shape informs the accuracy of 3D translation 403 between fluoroscopic views 407, 409. 3D fluoroscopic marker positions 401 may be determined for all fluoroscopic markers 301 located within the fluoroscopic imaging frame. Once 3D fluoroscopic marker positions 401 are determined for each fluoroscopic marker 301 located within the fluoroscopic imaging frame, 3D fluoroscopic marker positions 401 may then be translated onto CT scans to compare marker locations from fluoroscopic imaging and CT imaging.

Though described herein as utilizing two separate fluoroscopic imagers 416, 426, one of skill in the art will recognize that typically a clinician will only have a single fluoroscopic imager available. Accordingly, it should be understood that fluoroscopic imagers 416, 426 may be understood to refer to two locations of a single fluoroscopic imager.

Turning now to FIGS. 5A and 5B, a two-dimensional diagram view showing translating of fluoroscopic marker data to CT images in order to compare and register the marker data is shown. FIGS. 5A and 5B show fluoroscopic frame 510 and CT frame 530 (respectively). Fluoroscopic frame 510 includes 3D fluoroscopic marker positions 401, generated according to 2D marker locations 422 in second fluoroscopic image 420 and first fluoroscopic 2D marker location 412 in first fluoroscopic image 410 (not shown in FIGS. 5A and 5B).

CT frame 530 represents a 2D view of a 3D image generated by performing a CT scan. CT frame 530 includes target 303, which may be originally identified in the 3D CT scan image, and CT marker locations 531 representing locations of fluoroscopic markers 301 according to the location of fluoroscopic markers 301 when the CT scan is performed. CT frame 530 also includes a translated version of 3D fluoroscopic marker positions 401. 3D fluoroscopic marker positions 401 are translated into CT frame 530 using a method, describe in detail below, known as pose estimation. Once 3D fluoroscopic marker positions 401 are translated into CT frame 530, registration of CT marker locations 531 according to the translated 3D fluoroscopic marker positions 401 may be performed and CT marker locations 531 may be updated. After all are updated, the new locations may be used to update a model of the bronchial tree to provide real time feedback to a physician performing a procedure. Additionally, target error may be determined according to the translation distance of CT marker locations 531 during registration and position update.

Figure 6:
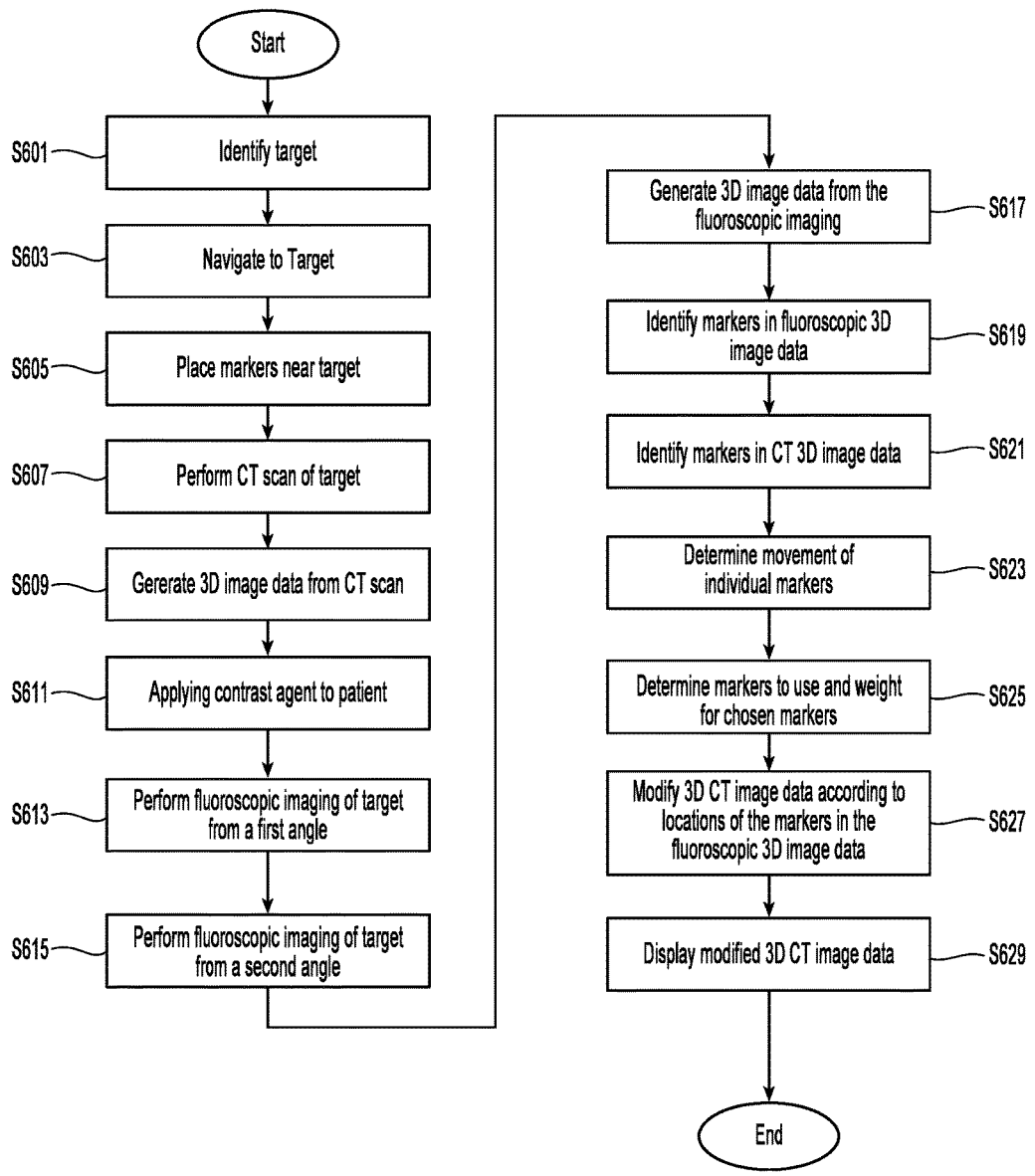
FIG. 6 is a flow chart of a method of placing the fluoroscopic markers of FIG. 3 and updating a CT model of a luminal network.

Turning to FIG. 6, there is shown a flow chart of a method of placing the fluoroscopic markers of FIG. 3 and updating a CT model of a luminal network. At step S601, a treatment target is identified. A target may be determined using pre-procedure CT images, MRI images, PET images, fluoroscopic images, or any other suitable imaging to determine a location of potentially problematic tissue within a patient. A physician may also navigate a sensor with a camera through the body and determine a treatment target through visual inspection of tissue.

Once a target is identified at step S601, a path through the branches of the airways to the target is generated in CT or other image data. Once the pathway plan has been developed and is accepted by the clinician, the pathway plan can be utilized in a navigation procedure using the EMN system 10. The pathway plan is loaded into an application on workstation 80 and displayed, allowing a physician to navigate LG 92 extending distally from bronchoscope 50 to a location near a treatment or biopsy target at step S603.

During navigation, application 81 may perform registration of the CT scan with the patient's airways, as described above, and in particular as described in co-pending U.S. patent application Ser. No. 14/790,581, entitled REAL TIME AUTOMATIC REGISTRATION FEEDBACK, filed on Jul. 2, 2015, by Brown et al., the entire contents of which is incorporated herein by reference. During registration, the location of EM sensor 94 within the patient's airways is tracked, and a plurality of points denoting the location of EM sensor 94 within the EM field generated by EM generator 76 is generated. When sufficient points have been collected, the application 81 compares the locations of these points to the 3D model and seeks to fit all the points within the lumens of the 3D model. When a fit is established, signifying that the majority if not all of the points have been fit within the area defined by the 3D model of the airway, the patient and the 3D model are registered to one another. As a result, detected movement of the EM sensor 94 within the patient can be accurately depicted on the display of the workstation 80 as a sensor 94 traversing the 3D model or a 2D image from which the 3D model was generated.

Upon reaching a point near the target, LG 92 is removed. Fluoroscopic markers 301 may then be inserted into the EWC 96 and advanced and ejected at a desired location using a guide wire 305. In the alternative, EWC may be excluded, in which case, guide wire 305 is guided directly through bronchoscope 50. Before placing guide wire 305 in the patient's airways through bronchoscope 50, fluoroscopic marker 301 is coupled to a distal end of guide wire 305. Guide wire 305 may include a gripping mechanism, a dissolvable adhesive, or other feature provided to couple fluoroscopic marker 301 to the distal end of guide wire 305 in a manner that allows for decoupling within a patient's body. Once the distal end of guide wire 305 reaches a point near the target, at step S605, fluoroscopic marker 301 is decoupled from guide wire 305 and lodges within the lungs. Fluoroscopic marker 301 may include a bonding agent or gripping ridges to bind fluoroscopic marker 301 to a wall of the luminal network. Fluoroscopic marker 301 may also have a shape designed to securely lodge fluoroscopic marker 301 in a lung branch. Fluoroscopic markers 301 are placed at several locations near the treatment target with a distribution sufficient to allow for an estimation of movement of a moveable area surrounding the treatment target.

Once all fluoroscopic markers 301 are placed, the patient undergoes another CT scan, at step S607. The scan concentrates on an area of interest of the patient, containing the treatment target and consequentially, fluoroscopic markers 301 which are usually near the treatment target. In the CT scan, the treatment target and fluoroscopic markers 301 are detected and can be shown or displayed on monitoring equipment 60. At step S609, 3D image data of the area of interest, the treatment target, and fluoroscopic markers 301 is generated and saved on a memory of computing device 80 or a network.

At step S611, preparation for fluoroscopic imaging begins. In some embodiments as an alternative to or in conjunction with fluoroscopic markers 301 a contrasting agent, possibly a contrast dye or iodine, is applied to the treatment target. The contrast agent creates a higher contrast for more detailed fluoroscopic imaging of tissue and allows a physician to view lung structure and features.

The patient is imaged at steps S613 and S615. Imaging is performed with fluoroscopic imaging device 201, positioned at poses with a known distance and/or angle between the poses. FIG. 4 depicts steps S613 and S615 occurring sequential with step S615 following step S613.

At step S617, fluoroscopic images generated in step S613 and S615 are compared according to the known pose angle and distance between the poses of fluoroscopic imaging device 201. Using the known orientations of fluoroscopic imaging device 201, application 81 may generate a 3D space. Then, the images generated in steps S613 and S615 are projected through the 3D space from fluoroscopic imaging device 201. Application 81 may produce 3D fluoroscopic image data representing the projections of the images of the fluoroscopic imaging devices 201. Alternatively, if application 81 identifies intersecting points between projections of the images of the fluoroscopic imaging devices 201, shown by a common pixel density aberration, such as a small group of saturated pixels, application 81 may determine the aberration represents a 3D image point of the imaged lungs. Application 81 may further compare pixel densities across the entirety of the intersection volume of the image projections to generate estimated 3D image data, with the estimation being anchored according to positions of identified pixel aberrations. 3D image data may further be generated by comparing the image projections to the CT scan or a general model of the lungs.

At step S619, the locations of the markers are determined in 3D space from the fluoroscopic images. Fluoroscopic markers 301 appear in the fluoroscopic images as lines of high brightness pixels. Therefore, a fluoroscopic marker 301 is easily identifiable in a fluoroscopic image. Application 81 locates lines of high brightness pixels and identified 2D locations of each fluoroscopic marker 301. Using the known poses and locations of fluoroscopic imaging device 201 and identified positions of fluoroscopic markers 301 in the 2D fluoroscopic images, application 81 determines 3D coordinates for fluoroscopic markers 301 using a process that is described further in FIG. 5.

At step S621, 3D locations of fluoroscopic markers 301 are determined in CT images generated at step S609. Determining locations of fluoroscopic markers 301 in a 3D CT model can be accomplished using known methods. Generally, application 81 will identify a line of high brightness pixels and determine that the pixel line represents a fluoroscopic marker.

At step S623, the locations of fluoroscopic markers 301 determined, at step S619, using the fluoroscopic images and the locations of fluoroscopic markers 301 determined at step S621, using the CT images are compared. Marker locations may be compared as a group according to a center of each set of markers location. Individual marker locations may also be compared. In such a circumstance, application 81 determines corresponding marker locations for comparison according to which markers locations have substantially similar 3D coordinates. Once corresponding marker locations have been determined, Application application 81 measures the distance between corresponding fluoroscopic image marker locations and the CT image marker locations. The distance between marker locations is determined to be movement of fluoroscopic markers 301 between the time the CT scan was performed and the fluoroscopic imaging was performed.

At step S625, application 81 determines the distances between markers in the fluoroscopic 3D image data and CT 3D image data. If the distance exceeds a predetermined amount or ratio, the marker is excluded from modification of 3D CT image data. Additionally, markers that are not excluded may be weighted according to their distance from the target. Weighing may be established according to a general equation based on the distance from the target or a physician may determine how to weight the markers.

At step S627, application 81 modifies the 3D CT image data according to the locations of the markers in the 3D image data. Markers excluded at step S625 are not used to update and modify the 3D CT image data. Application 81 may modify the 3D CT image data according to weights established in step S625. The modified 3D CT image data is then used to update the 3D model of the luminal network.

Finally, at step S629, the updated 3D model and/or CT image data including updated marker locations is displayed. The displayed 3D model and/or CT image data may be used to update or plan a path to navigate to the treatment target. The displayed 3D model and/or CT image data may also provide guidance while a physician is navigating a tool to a treatment target.

Figure 7:
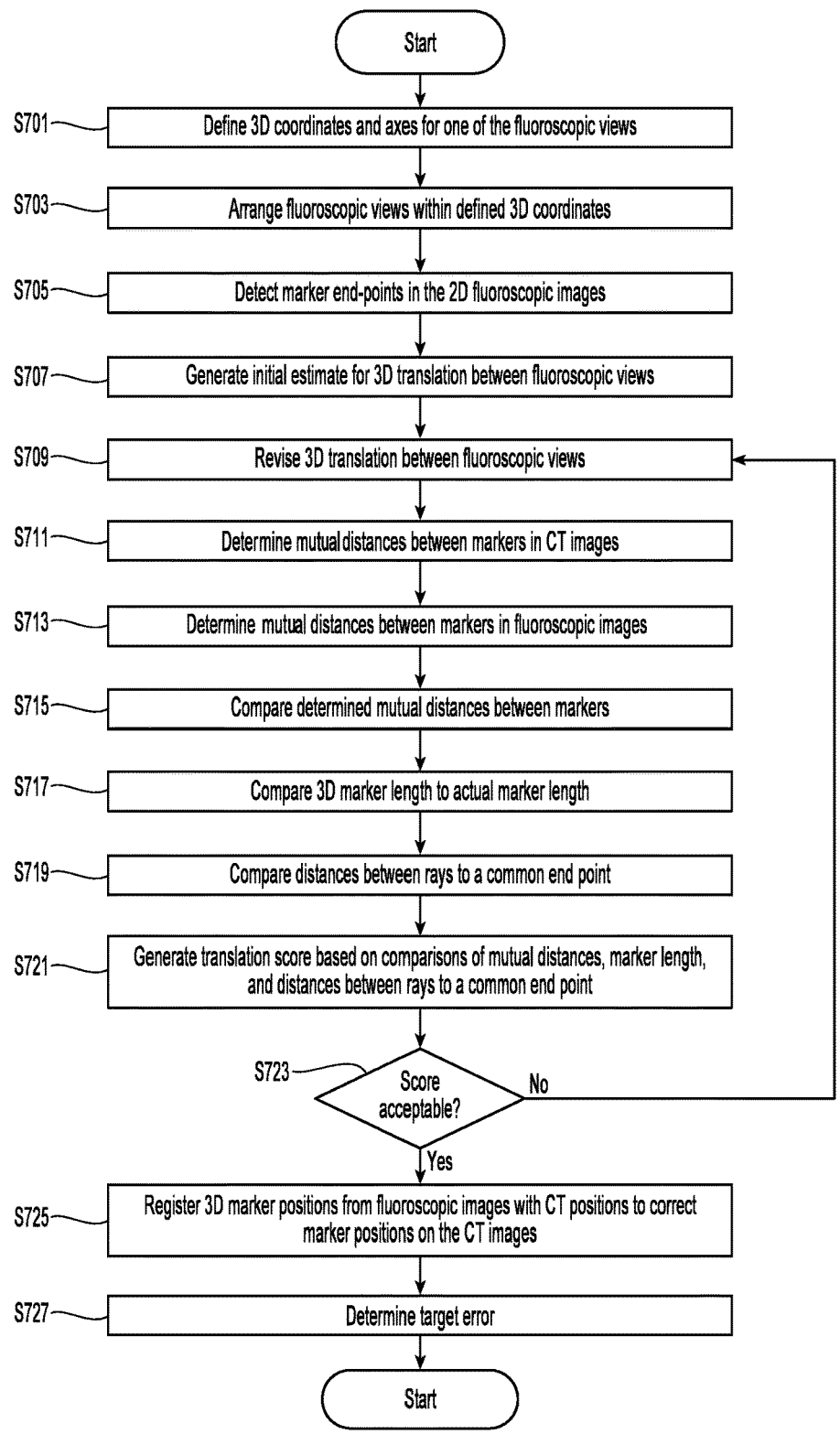
FIG. 7 is a flow chart of a method of locating 3D marker locations in an intersection of fluoroscopic images projections and updating a CT model of a luminal network according to marker locations in the fluoroscopic images.

Turning now to FIG. 7, there is shown a flow chart of a method of locating 3D marker locations in an intersection of fluoroscopic images projections and updating a CT model of a luminal network according to marker locations in the fluoroscopic images. The process begins at step S701. At step S701, application 81 generates first 3D space and axes for establishing a coordinate system to define the 3D space for a first fluoroscopic view. Within the 3D space, relative positions for 2D first fluoroscopic image 410 and first fluoroscopic imager 416 which generates first fluoroscopic image 410 are established. Because an imaging depth is difficult to determine and 3D translation 403 between poses of fluoroscopic imagers 416, 426 is not known, the position and size of 2D first fluoroscopic image 410 and the position of first fluoroscopic imager 416 in the 3D space is set according to initial, assumed reasonable values for image diameter, pixel-to-mm ratio and source-to-image-distance. Image diameter establishes the size of first fluoroscopic image 410 in the 3D space; pixel-to-mm ratio establishes brightness density according to the distance and image diameter; and source-to-image-distance establishes a distance between first fluoroscopic image 410 and first fluoroscopic imager 416. The axes' origin may be determined arbitrarily, though in practice, the origin may conveniently be placed approximate a midpoint of first fluoroscopic image 410 and first fluoroscopic imager 416.

At step S703, application 81 determines a relative 3D positioning between 2D second fluoroscopic image 420 and fluoroscopic imager 426 and determines a size of fluoroscopic image 420 according to initial, assumed reasonable values for image diameter, pixel to mm ratio and source-to-image-distance. The assumed values may, but need not, be the same or approximately the same as the assumed reasonable values in step S701.

Angle 405 between poses of the first and second fluoroscopic views is a known value. A user or robotic system may establish angle 405 by positioning fluoroscopic imagers 416, 426 at an intended orientation with respect to one another. Lower angle values as well as angle values near 180 degrees reduce the precision of results of the current process. Given angle 405, application 81 orients second fluoroscopic view, including second fluoroscopic image 420 and fluoroscopic imager 426, at a position with a 3D rotation that corresponds to angle 405. Once the first and second poses are oriented with the 3D rotation that corresponds to angle 405, estimated locations within the 3D space for the fluoroscopic markers are defined according to the coordinate system established in step S701. However, 3D translation 403 between poses of fluoroscopic imagers 416, 426 remains undetermined.

Figure 5:
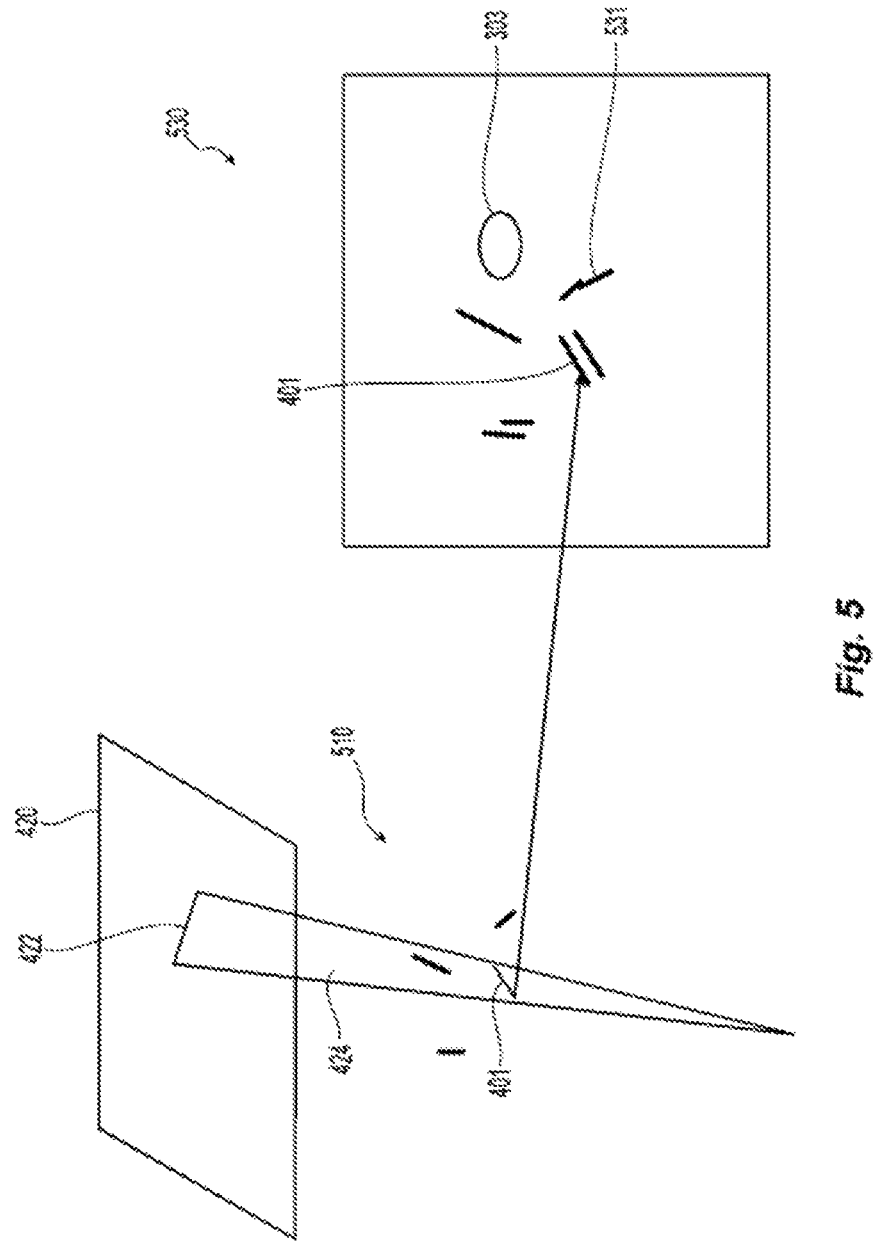
FIG. 5 is two-dimensional diagram view showing translating of fluoroscopic marker data to CT images order to compare and register the marker data.

At step S705, application 81 identifies fluoroscopic 2D marker locations 412, 422 of fluoroscopic markers 301 within first fluoroscopic image 410 and second fluoroscopic image 420. Application 81 scans fluoroscopic images 410, 420 searching for bright portions of the image having a shape the same as or similar to a shape as the fluoroscopic markers 301, these are shown in FIG. 5 as a rod or line. The bright portions may be determined by scanning pixel values of image data of fluoroscopic images 410, 420 and locating a grouping of high brightness pixels. Alternatively, image processing software known in the art may be used so measure a bright portion of fluoroscopic images 410, 420 and determine a shape of the bright portion. Once fluoroscopic 2D marker locations 412, 422 are established, application 81 determines endpoints of fluoroscopic 2D marker locations 412, 422. Endpoints are determined by finding a marker edges, either through image recognition or by determining that a line of bright pixels is adjacent dim or at least dimmer pixels, comparing the edges, and establishing a point on each of two marker edges that have a greatest distance between them. Upon determining endpoints of a fluoroscopic 2D marker locations 412, 422, application 81 assigns 3D coordinates to the endpoints according to the location of the endpoints within the coordinate system. The 3D endpoint coordinates may therefore be used to define locations of fluoroscopic 2D marker locations 412, 422 on fluoroscopic images 410, 420 within the 3D space. After establishing 3D coordinates defining fluoroscopic 2D marker locations 412, 422, a correspondence between each first fluoroscopic 2D marker location 412 and each second fluoroscopic 2D marker location 422 is established according to the angle 405. Each pair of corresponding marker locations represents projections of a single fluoroscopic marker 301.

As an alternative to determining corresponding marker locations using angle 405, application 81 may perform a pose estimation procedure according to CT marker location 531. A pose estimation procedure, includes determining fluoroscope projection angles, focal point, and zoom relative to the 3D CT model generally includes extracting CT data and overlaying it on the fluoroscopic image. The process of determining fluoroscope projection angles, focal point, and zoom is more fully described in commonly-owned U.S. patent application Ser. No. 14/725,300, entitled "Fluoroscopic Pose Estimation," filed on May 29, 2015, by Merlet, the entire contents of which are hereby incorporated by reference.

While 3D rotation between fluoroscopic views was previously determined at step S703, 3D translation 403, has not yet been established. Establishment of 3D translation 403 between the fluoroscope views is necessary to align fluoroscopic projection 414, 424 to determine 3D fluoroscopic marker positions 401 in 3D space. At step S707, application 81 generates an initial estimate of 3D translation 403. Application 81 determines the center of mass for first fluoroscopic 2D marker locations 412 and a center of mass for second fluoroscopic 2D marker location 422. In order to find the centers of mass, each marker is weighted equally and the x, y, and z coordinates along the lengths of the fluoroscopic 2D marker locations 412, 422 are averaged. To simplify the procedure, the endpoints of fluoroscopic 2D marker locations 412, 422 may be used. Once the centers of mass are established, application 81 translates the fluoroscopic views in the 3D space such that a projection ray between first fluoroscopic imager 416 and the center of mass of first fluoroscopic 2D marker locations 412 intersects a projection ray between second fluoroscopic imager 426 and the center of mass of second fluoroscopic 2D marker location 422. Application 81 further translates the fluoroscopic views in the 3D space so that the distances between the intersection of the projected rays and each fluoroscopic imager 416, 426 are substantially equal.

As an alternative to generating an initial estimate using a center of gravity, application 81 may perform pose estimation to develop the initial estimate of 3D translation 403. Pose estimation is performed for each fluoroscopic view. The pose estimate matches CT marker location 531 with fluoroscopic 2D marker locations 412, 422 and translates, as the initial estimate, the fluoroscopic views according to the result of the pose estimation.

At step S709, 3D translation 403 is revised. 3D translation 403 can be described by lengths (Tx, Ty, Tz). Revision to 3D translation 403 may come in a variety of forms. Primarily, at step S709, application 81 adjusts Tx, Ty, Tz values individually by a small amount, though a combination of Tx, Ty, Tz values may be adjusted. Once an adjustment to 3D translation 403 is set, application 81 generates first fluoroscopic projection 414 and second fluoroscopic projection 424 for each pair of corresponding marker locations and determines 3D fluoroscopic marker position 401 for each pair. Once 3D fluoroscopic marker positions 401 are determined for all fluoroscopic markers 301, the process proceeds to steps S711-S719 to determine the accuracy of 3D translation 403.

At steps S711-S715, application 81 develops mutual distances between marker locations in CT images from CT frame 530 by measuring distances between each CT marker location 531 and every other CT marker location 531 and between each 3D fluoroscopic marker position 401 and every other 3D fluoroscopic marker position 401. For purposes of simplifying the calculation, application 81 may determine a center point for each CT marker location 531 and each 3D fluoroscopic marker position 401, thereby allowing distances between marker locations within a single imaging frame, fluoroscopic frame 510 or CT frame 530, to be determined by subtracting x, y, and z coordinates of marker location center points. At step S715, the mutual distances between markers are compared across imaging frames. This comparison relies on the general understanding that between the time of the CT scan and fluoroscopic imaging, fluoroscopic markers 301 may have moved, but they likely moved proportionally to or in tandem with one another. If application 81 determines that one of the determined mutual distances associated with one 3D fluoroscopic marker position 401 is substantially greater than other mutual distances in either frame 510, 530, the mutual distance associated with that 3D fluoroscopic marker position 401 may be ignored for purposes of comparing mutual distances.

At step S717, application 81 determines coordinates of endpoints of 3D fluoroscopic marker positions 401. For each 3D fluoroscopic marker position 401, application 81 subtracts the x, y, z, coordinates of the endpoints to determine the lengths of 3D fluoroscopic marker positions 401. The lengths are then compared against a known length of fluoroscopic markers 301 to determine an accuracy of 3D fluoroscopic marker positions 401.

At step S719, application 81 determines distances between first fluoroscopic imager 416 and each endpoint of first fluoroscopic 2D marker locations 412 and distances between second fluoroscopic imager 426 and each endpoint of second fluoroscopic 2D marker locations 422. Then, application 81 compares the determined distances associated with opposing endpoints of each pair of corresponding marker locations.

At step S721, application 81 registers the results from the comparisons of mutual distances, marker length, and distances between rays to a common end point. Using these comparisons, application 81 develops a numerical score. The numerical score may be determined according to a cumulative calculation wherein each comparison receives an individual score and the individual scores are summed. Individual comparison scores may additionally be weighted prior to calculating a summed score. Alternatively, the numerical score may be determined based on each comparison considered simultaneously, the result of each comparison informing and determining an impact of each of the other comparisons. Once a score is determined, at step S723, application 81 or a user determines whether the numerical score is acceptable.

Determining acceptability of the numerical score may, for example, include comparing the score against predetermined threshold value, with or without an error factor. As an additional example, determining acceptability may include presenting the user with the score to allow the user to determine whether the score is acceptable. As a final but not conclusive example, the acceptability of the score may be determined according to previously determined scores. As the process iterates through steps S709-S721, application 81 determines a score for each revision of the 3D translations. This process allows for a sweeping of 3D translation values to determine 3D translation values at which the numerical score is at or near its lowest possible value. To accomplish such a sweep, application 81 may determine if a sufficient number of iterations have been performed or if progressive scores have ceased to improve substantially. If application 81 determines that the score is not improving substantially or if application 81 determines that a sufficient, or predetermined, number of iterations have been performed and that the score is at the lowest value among the iteration scores, application 81 may determine that the score is acceptable.

If the score is determined to be acceptable, the process continues to step S725. Otherwise, the process returns to step S709 and the process iterates through steps S709-S723 until an acceptable score is realized.

Moving on to step S725, application 81 performs registration of 3D fluoroscopic marker locations 401 from fluoroscopic images 410 to CT marker locations 531 to correct CT marker locations 531 so that CT marker locations 531 accurately reflect the true, up-to-date positions of fluoroscopic markers 301. To perform the registration, application 81 performs a pose estimation procedure as described in previously reference and incorporated application Ser. No. 14/725,300. The pose estimation procedure solves for a rotation angle and translation coordinates in order to overlay 3D fluoroscopic marker locations 401 within CT frame 530. Once 3D fluoroscopic marker locations 401 and CT marker locations 531 are both translated into and displayed in CT frame 530, CT marker locations are modified according to the translated 3D fluoroscopic marker locations 401.

Registration of 3D fluoroscopic marker locations 401 to CT marker locations 531 may be performed in a variety of manners. For example, all 3D fluoroscopic marker locations 401 may be given equal weight. Accordingly, CT marker locations 531 may be relocated to corresponding positions of 3D fluoroscopic marker locations 401. Additionally, instead of moving CT marker locations 531 to the exact locations of 3D fluoroscopic marker locations 401, a center of gravity of 3D fluoroscopic marker locations 401 and of CT marker locations 531 may be determined and CT marker locations 531 may be shifted such that their center of gravity becomes the same as the center of gravity of 3D fluoroscopic marker locations 401. As another alternative, the center of gravity of CT marker locations 531 may shift toward the center of gravity of 3D fluoroscopic marker locations 401, but stop short of fully relocating to the position.

The registration may also apply unequal weight to 3D fluoroscopic marker locations 401. For example, application 81 may determine distances between 3D fluoroscopic marker locations 401 and corresponding CT marker locations 531. If a distance for one or more corresponding markers is greater than a certain threshold or percentage value, application 81 may determine that that particular marker may have dislodged and migrated. Registration using a marker that has migrated would disturb the updated positions and create an inaccurate result. Therefore, if a distance for one or more corresponding markers is greater than a certain threshold or percentage value, the specific 3D fluoroscopic marker locations 401 may be excluded. Then, registration is performed as usual according to previously discussed methods or methods commonly known in the art.

The registration may also apply varied weights to 3D fluoroscopic marker locations 401 without excluding any 3D fluoroscopic marker locations 401. 3D fluoroscopic marker locations 401 may be assigned a weight according to their proximity to target 303. Weighting of 3D fluoroscopic marker locations 401 may generate a better registration at target 303 as fluoroscopic markers 301 will tend to move in closer relation to the movement of target 303. After weighting, registration is performed as usual according to previously discussed methods or methods commonly known in the art.

The new CT marker locations may then be used to update a previously developed model of the lungs. Updates to the model may occur in real time as the patient is imaged using fluoroscopic imaging. Continual updates to the model provide increased accuracy to the model and aid a physician's ability to accurately track treatment target 303 while performing a surgical procedure at target 303.

At step S727, application 81 determines a target error based on a comparison of CT marker locations 531 before and after the registration. Certain CT marker locations 531 may be excluded from the calculation of target error if a distance between a specific CT marker location 531 before and after the registration is large so as to indicate that the specific CT marker location 531 has migrated. In order to determine the target error, the shift distance by CT marker locations 531 before and after the registration is compared against the 3D location of the original CT position with respect to target 303.

Figure 8:
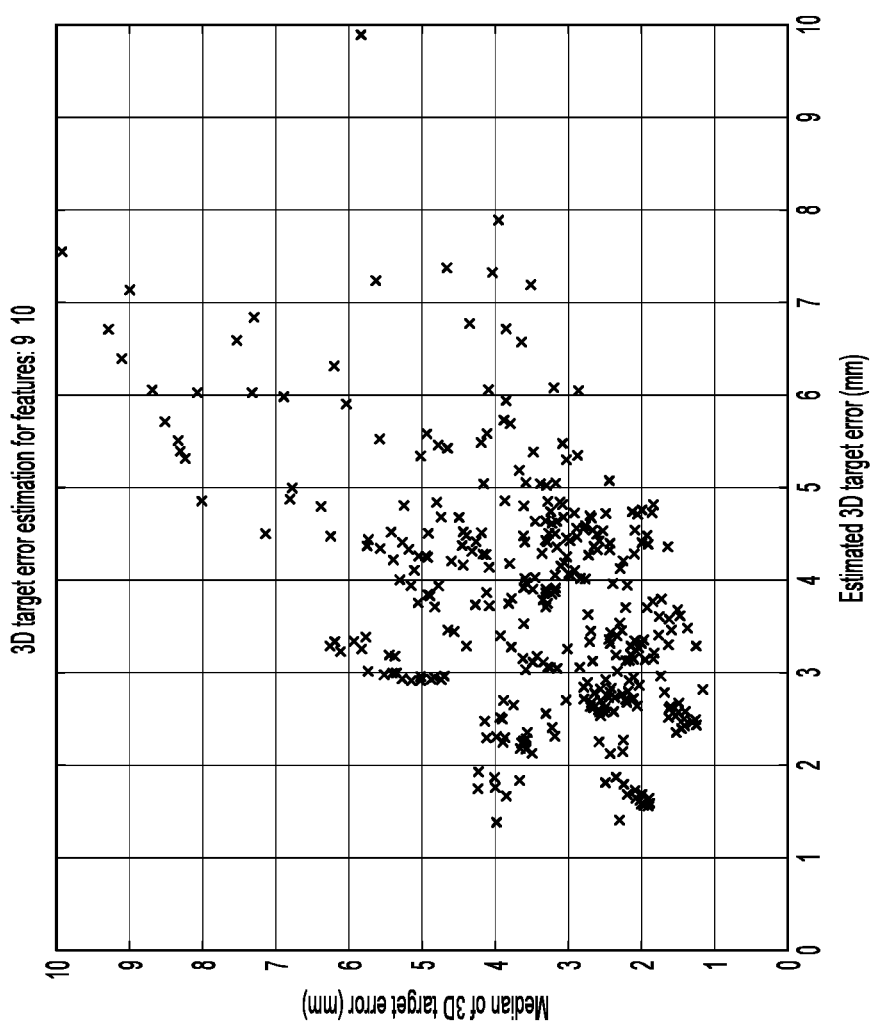
FIG. 8 is a graph presenting exemplary data of true target error in 3D as a function of the estimated target error.

Turning now to FIG. 8, there is shown a graph presenting exemplary data of true target error in 3D as a function of the estimated target error for four fluoroscopic markers. The graph shows that as the estimated 3D target error decreases, the variance in median 3D target error also decreases. Therefore, when the estimated 3D target error is low, a physician performing the processes of the current application may more closely rely on the results of the procedure. If a physician is not satisfied with the potential median 3D target error for a given estimated 3D target error, the physician may choose to re-perform the procedure. Such a determination may depend on conditions such as size of the treatment target, length of time for performing treatment on the target, type of tissue and a number of other similar considerations.

Figure 9:
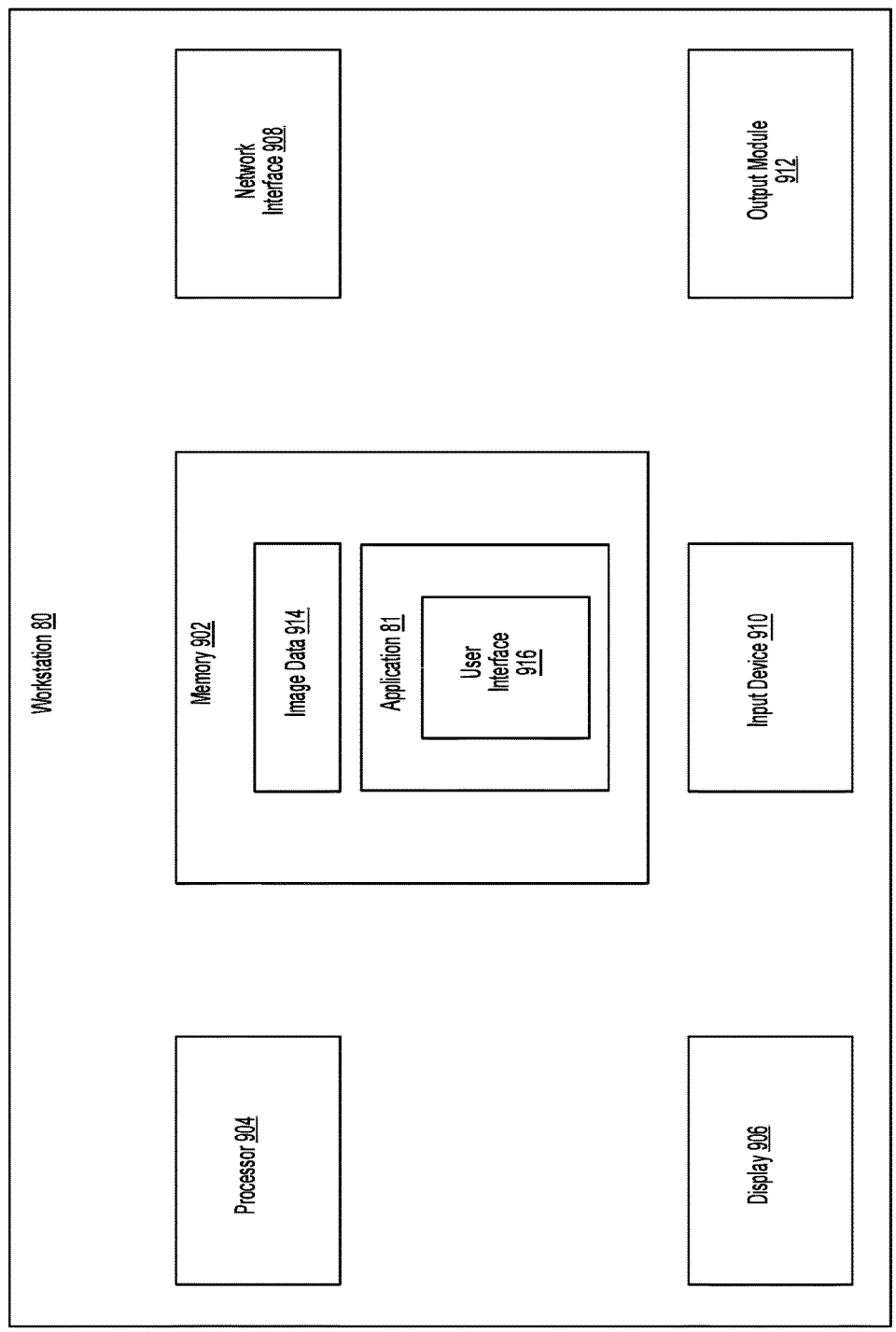
FIG. 9 is a schematic block diagram of a workstation configured for use with the system of FIG. 1.

Turning now to FIG. 9, there is shown a system diagram of workstation 80. Workstation 80 may include memory 902, processor 904, display 906, network interface 908, input device 910, and/or output module 912.

Memory 902 includes any non-transitory computer-readable storage media for storing data and/or software that is executable by processor 904 and which controls the operation of workstation 80. In an embodiment, memory 902 may include one or more solid-state storage devices such as flash memory chips. Alternatively or in addition to the one or more solid-state storage devices, memory 902 may include one or more mass storage devices connected to the processor 904 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 904. That is, computer readable storage media includes non-transitory, volatile and non-volatile, removable and non-removable media implemented in any method or technology for storage of information such as computer-readable instructions, data structures, program modules or other data. For example, computer-readable storage media includes random-access memory (RAM), read-only memory (ROM), erasable programmable read-only memory (EPROM), electrically erasable programmable read-only memory (EEPROM), flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 902 may store application 81 and/or CT image data 914. Application 81 may, when executed by processor 904, cause display 906 to present user interface 916. Network interface 908 may be configured to connect to a network such as a local area network (LAN) consisting of a wired network and/or a wireless network, a wide area network (WAN), a wireless mobile network, a Bluetooth™ network, and/or the internet. Input device 910 may be any device by means of which a clinician may interact with workstation 80, such as, for example, a mouse, keyboard, foot pedal, touch screen, and/or voice interface. Output module 912 may include any connectivity port or bus, such as, for example, parallel ports, serial ports, universal serial busses (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

Detailed embodiments of such devices, systems incorporating such devices, and methods using the same are described above. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the example embodiments described above are directed to the bronchoscopy of a patient's airways, those skilled in the art will realize that the same or similar devices, systems, and methods may also be used in other lumen networks, such as, for example, the vascular, lymphatic, and/or gastrointestinal networks.

What is claimed is:

1. A method of updating a model of a luminal network, comprising:
   generating 3D image data including fiducial markers disposed at a first location using images captured in a first imaging of a target;
   generating 2D image data including the fiducial markers disposed at a second location using images captured in a second imaging of the target, the second imaging of the target including imaging of the target from a first viewpoint and imaging the target from a second viewpoint, the first and second viewpoints oriented at a known angle relative to each other;
   determining the second location of the fiducial markers in 3D space based on the second location of the fiducial markers within the 2D image data of the first viewpoint, the second location of the fiducial markers within the 2D image data of the second viewpoint, and the known angle;
   comparing the first location of the fiducial markers in the 3D image data to the second location of the fiducial markers in 3D space;
   determining a difference between the first location of the fiducial markers in the 3D image data and the second location of the fiducial markers in 3D space based on the comparison;
   updating the 3D image data generated using images captured in the first imaging with the determined second location of the fiducial markers in 3D space based on the determined difference;
   displaying the updated 3D image data including the fiducial markers disposed at the second location of the fiducial markers in 3D space;
   determining movement distances between the second location of the fiducial markers in 3D space and the first location of the fiducial markers in the 3D image data from the first imaging;
   determining which of the movement distances exceeds a threshold; and registering the 3D image data generated using images captured in the first imaging with the determined second location of the fiducial markers in 3D space, wherein the registering excludes the second location in 3D space of the fiducial marker corresponding to movement distances that exceed the threshold.

2. The method of claim 1, wherein the first imaging is performed using CT imaging.

3. The method of claim 1, wherein the second imaging is performed using fluoroscopic imaging.

4. The method of claim 1, wherein determining the second location of the fiducial markers in 3D space includes:
projecting rays from the first viewpoint through endpoints of each of the fiducial markers,
projecting rays from the second viewpoint through the endpoints of each of the fiducial markers; and
determining intersections of the rays projected from the first viewpoint and the rays projected from the second viewpoint as locations of fiducial marker endpoints in 3D space.

5. The method of claim 4, further comprising:
determining a distance between adjacent fiducial marker endpoints; and
comparing the distance between adjacent fiducial marker endpoints with a known length of at least one of the fiducial markers.

6. A system comprising:
a display configured to display:
3D image data of a target, the 3D image data including fiducial markers disposed at a first location;
first 2D image data of the target imaged from a first viewpoint; and
second 2D image data of the target imaged from a second viewpoint, the second viewpoint oriented at a known angle from the first viewpoint, the first 2D image data and the second 2D image data including the fiducial markers disposed at a second location;
a computing device including a processor and a memory storing instructions which, when executed by the processor, cause the computing device to:
determine the second location of the fiducial markers in 3D space according to the second location of the fiducial markers within the first 2D image data, the second location of the fiducial markers within the second 2D image data, and the known angle;
compare the first location of the fiducial markers in the 3D image data to the second location of the fiducial markers in 3D space;
determine a difference between the first location of the fiducial markers in the 3D image data and the second location of the fiducial markers in 3D space;
update the 3D image data with the determined second location of the fiducial markers in 3D space based on the determined difference;
display the updated 3D image data including the fiducial markers disposed at the second location of the fiducial markers in 3D space via the display;
determine movement distances between the second location of the fiducial markers in 3D space and the first location of the fiducial markers in the 3D image data;
determine which of the movement distances exceeds a threshold; and
register the 3D image data generated using images captured in the first imaging with the determined second location of the fiducial markers in 3D space, wherein the registration excludes the second location in 3D space of the fiducial marker corresponding to movement distances that exceed the threshold.

7. The system of claim 6, wherein the 3D image data is generated using CT imaging.

8. The system of claim 6, wherein the first 2D image data and the second 2D image data are generated using fluoroscopic imaging.

9. The system of claim 6, wherein in the determination of the second location of the fiducial markers in 3D space, the instructions further cause the computing device to:
project rays from the first viewpoint through endpoints of each of the fiducial markers;
project rays from the second viewpoint through the endpoints of each of the fiducial markers; and
determine intersections of the rays projected from the first viewpoint and the rays projected from the second viewpoint as locations of fiducial marker endpoints in 3D space.

10. The system of claim 9, wherein the instructions further cause the computing device to:
determine a distance between adjacent fiducial marker endpoints, and
compare the distance between adjacent fiducial marker endpoints with a known length of at least one of the fiducial markers.

11. A method of updating a 3D model of a luminal network, comprising:
generating a 3D model of a luminal network of a patient based on CT imaging of a target and at least one fiducial marker disposed at a first location relative to the target;
generating 2D image data based on fluoroscopic imaging of the target and the at least one fiducial marker from a first viewpoint and fluoroscopic imaging of the target and the at least one fiducial marker from a second viewpoint orientated at a known angle relative to the first viewpoint;
determining a second location of the at least one fiducial marker in 3D space based on a second location of the at least one fiducial marker within the 2D image data;
determining a difference between the first location of the at least one fiducial marker in the CT imaging of the luminal network and the second location of the at least one fiducial marker in 3D space;
updating the 3D model of the luminal network based on the determined difference between the first location of the at least one fiducial marker in the CT imaging of the luminal network and the second location of the at least one fiducial marker in 3D space;
displaying the updated 3D model of the luminal network including the at least one fiducial marker disposed at the second location of the at least one fiducial marker in 3D space;
determining movement distances between the second location of the fiducial marker in 3D space and the first location of the fiducial marker in the CT imaging;
determining which of the movement distances exceed a threshold; and
registering the 3D model generated using images captured in the CT imaging with the determined second location of the fiducial markers in 3D space, wherein the registering excludes the second location in 3D space of the fiducial marker corresponding to movement distances that exceed the threshold.

* * * * *